(12) United States Patent
Skocic

(10) Patent No.: US 11,482,310 B1
(45) Date of Patent: Oct. 25, 2022

(54) ANIMAL DATA MANAGEMENT

(71) Applicant: MLP Technology Inc., Hiram, OH (US)

(72) Inventor: Ruth E. Skocic, Hiram, OH (US)

(\*) Notice: Subject to any disclaimer, the term of this patent is extended or adjusted under 35 U.S.C. 154(b) by 307 days.

(21) Appl. No.: 16/830,856

(22) Filed: Mar. 26, 2020

Related U.S. Application Data

(63) Continuation of application No. 14/015,305, filed on Aug. 30, 2013, now abandoned, which is a continuation of application No. 13/294,476, filed on Nov. 11, 2011, now abandoned.

(60) Provisional application No. 61/412,662, filed on Nov. 11, 2010.

(51) Int. Cl.
  *G06F 21/62* (2013.01)
  *G16H 10/60* (2018.01)
  *A01K 11/00* (2006.01)

(52) U.S. Cl.
  CPC .......... *G16H 10/60* (2018.01); *A01K 11/006* (2013.01); *G06F 21/6218* (2013.01)

(58) Field of Classification Search
  CPC .... G16H 10/60; A01K 11/006; G06F 21/6218
  See application file for complete search history.

(56) References Cited

U.S. PATENT DOCUMENTS

| | | | | |
|---|---|---|---|---|
| 6,285,780 B1* | 9/2001 | Yamakita | ............. | A01K 11/006 382/110 |
| 7,328,276 B2* | 2/2008 | Alisuag | ................ | H04L 69/329 705/76 |
| 2003/0229452 A1* | 12/2003 | Lewis | ................... | A01K 11/006 702/19 |
| 2004/0150528 A1* | 8/2004 | Natividade | .......... | A01K 11/008 340/573.3 |
| 2006/0143302 A1* | 6/2006 | Welsh | .................... | G06Q 50/26 709/229 |
| 2007/0033215 A1* | 2/2007 | Heinle | ................. | G06Q 10/087 705/28 |
| 2007/0033216 A1* | 2/2007 | Heinle | ................... | G06Q 10/10 707/999.102 |
| 2007/0046476 A1* | 3/2007 | Hinkamp | ............... | A61B 5/117 340/573.1 |
| 2007/0226257 A1* | 9/2007 | Yarnall, Jr. | ............ | G06Q 10/10 |
| 2007/0288759 A1* | 12/2007 | Wood | ................... | G06Q 20/341 713/186 |
| 2008/0040157 A1* | 2/2008 | Saunders | ............... | G06Q 10/10 705/3 |
| 2009/0048867 A1* | 2/2009 | Soejima | ................. | G16H 40/67 705/2 |
| 2009/0070148 A1* | 3/2009 | Skocic | ................... | G06Q 10/10 705/3 |
| 2009/0256711 A1* | 10/2009 | Chao Cheng | ........ | A01K 11/006 340/573.3 |
| 2010/0148927 A1* | 6/2010 | De Meulemeester | ...................... | A01K 11/006 345/168 |

(Continued)

*Primary Examiner* — Khoi V Le
(74) *Attorney, Agent, or Firm* — Gugliotta & Gugliotta LPA

(57) ABSTRACT

Animal data is stored in memory accessible to a server. The server allows users to access the animal data, such as across a communication network. In some embodiments an identifier for an animal is stored with animal information. The identifier can be used to control access to animal records and to quickly locate animal information associated with a particular animal.

13 Claims, 10 Drawing Sheets

(56) References Cited

U.S. PATENT DOCUMENTS

2011/0142286 A1\* 6/2011 Morriyama ........ H04N 5/23218
                                                    382/103

\* cited by examiner

ANIMAL DATA MANAGEMENT

TECHNICAL FIELD

The present invention relates to a data management system, and more specifically, to a data management system allowing for storing, managing and transmitting information for animals as well as a method for such storage, management and transmission.

BACKGROUND

Health records for animals are usually maintained by an animal's veterinarian/health clinic describing the medical history of the animal, immunization records and the like. Breeding animals and show animals require different kinds of certificates and documents showing e.g. genealogy. Thus, pets and other animals require some paperwork, which usually is kept at the veterinary or animal health clinic or kept in the owner's home.

Moreover, when people travel with their pets such as on a vacation, they do not typically bring their pet's medical or health records since these documents are often not considered to be necessary for traveling. Thus, when an animal is injured or has some other medical emergency, proper medical attention may be delayed until the medical records of the animal are obtained from its primary veterinarian, or medical treatment may have to be provided absent the medical records. When a lost or injured animal is found, the animal rescue team and the veterinarian have no way of knowing the animal's history or existing condition and how to find the owner. Even if there is no question about how to treat the animal, preferences or desires of the owner are not known. The owner might want to save the animal at all costs no matter how badly injured it is, or the owner may wish to euthanize the animal if it is badly injured.

Lost or runaway animals are hard to track. Sometimes these animals are left at animal shelters and there is no way of finding the owner. It is up to the owner to contact different shelters, animal hospitals or the police to find a lost animal. When a disaster occurs, animals are often separated from their owners. The owners may end up in one shelter/relocation center and the animal may end up in an animal shelter. For persons with disabilities having a disability assistant animal it is important to reunite such an animal with the owner.

SUMMARY

In general terms, this disclosure is directed to animal data management. In one possible configuration and by non-limiting example, different kinds of animal information, including health information, is associated with an identifier, such as a biometric identifier or vitruvian identifier, of an animal. The identifier is used to access the animal information.

One aspect is an animal data management system comprising a server arranged to register an animal by receiving animal data including a first biometric or vitruvian identifier. The system also includes a memory for storing the animal data and the first biometric or vitruvian identifier in a database contained therein and associating the first biometric or vitruvian identifier with the animal data in the database, and for receiving information pertaining to the animal and storing that information in the database. The system further includes a user computing system arranged to send a request including a second biometric or vitruvian identifier to the server. The server includes a processor arranged to search the database to identify the first biometric or vitruvian identifiers a match to the second biometric or vitruvian identifier. A communication system is arranged to transmit at least part of the animal data associated with the first biometric or vitruvian identifierto the user computing system in response to the request.

Another aspect is a method of managing an animal data management system. An animal is registered as a registered animal in a database by storing animal data including a first identifier associated with the registered animal in the database. The method then stores the animal data and the first identifier in the database and associates the first identifier with the animal data in the database. Information pertaining to the animal is received and stored in the database. Upon occurrence of an event, a request including a second identifier is received from a user computing system. A search in the database is performed to identify the first identifier as a match to the second identifier. At least part of the animal data associated with the first identifier is transmitted to the user computing system in response to the request.

Still another aspect is a method of responding to a mass casualty situation and handling animals during the mass casualty situation. During a preparation period, the method comprises the steps of registering an animal by receiving animal data including a first biometric or vitruvian identifier, and storing the animal data and the first biometric or vitruvian identifier in a database and associating the first biometric or vitruvian identifier with the animal data in the database. During the mass casualty situation, the method comprises the steps of establishing a communication central for coordinating work between a plurality of emergency response functions, connecting the communication central to a server device including a processor and memory, the memory including the database comprising information pertaining the animal data and the biometric or vitruvian identifier, and searching the database to identify a found animal by matching the biometric or vitruvian identifier of the animal with the biometric or vitruvian identifier of an animal stored in the database.

DETAILED DESCRIPTION

Figure 1:
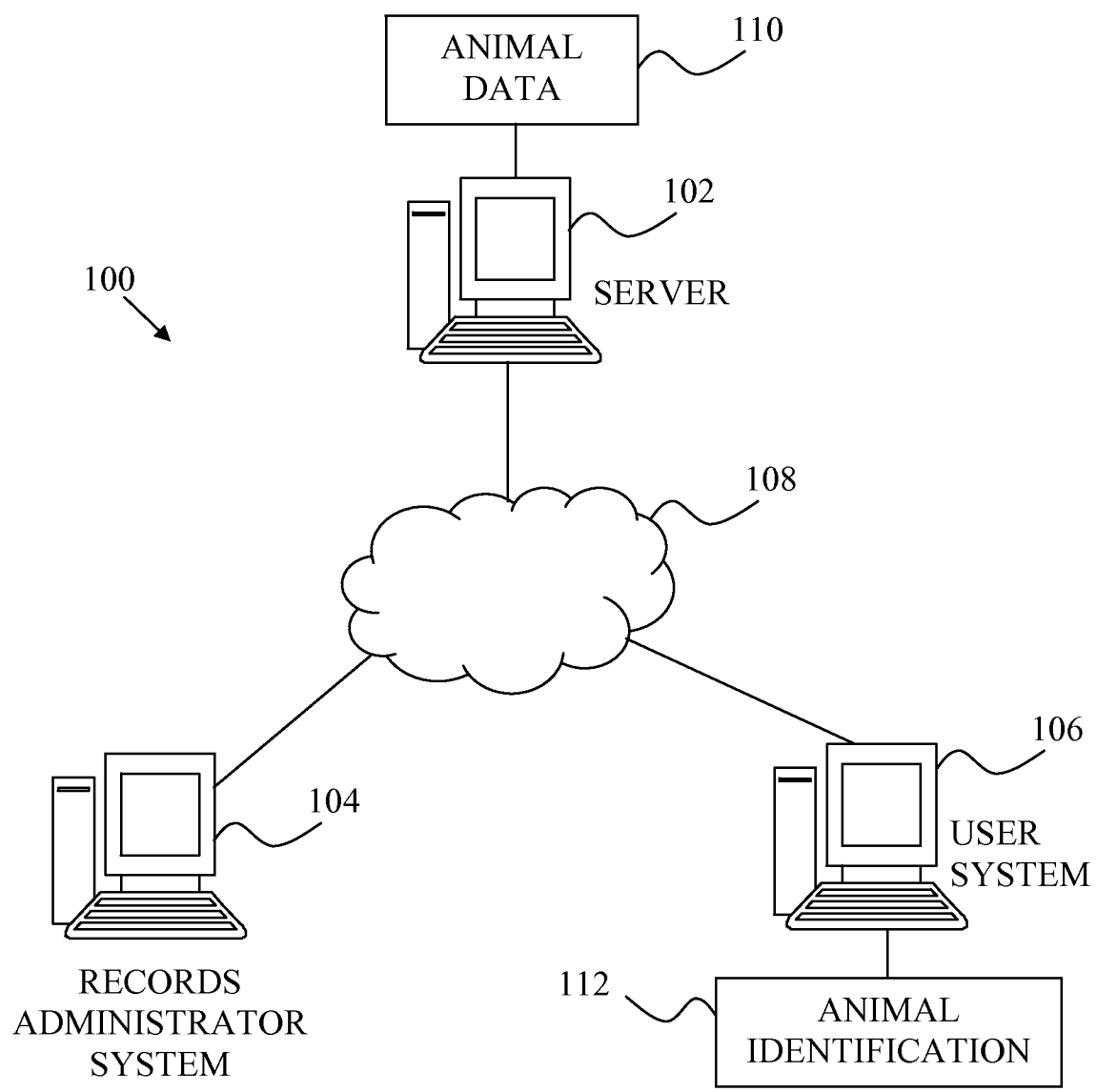
FIG. 1 is a schematic block diagram of an exemplary animal data management system according to the present disclosure.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

FIG. 1 is schematic block diagram of an exemplary animal data management system 100. System 100 includes server 102, records administrator computing system 104, and user computing device 106. In some embodiments communication occurs across network 108. Server 102 includes animal data 110. An animal identification device 112 is coupled to user computing device 106.

Briefly, some embodiments of animal data management system 100 operate to provide quick and convenient access to animal data 110, while protecting the privacy of animal data 110 from unauthorized access. For example, health records of an animal, such as a pet, horse, or any animal that would be desired to track and/or identify, are stored in animal data 110 of server 102.

Some embodiments of animal data management system 100 include some or all of the following.

Server 102 is a computing system that stores or is able to access animal data 110. Server 102 is in data communication with network 108. In some embodiments server 102 is a Web server that generates data for one or more web pages. The data is communicated across network 108 to a computing system operating a browser software application. An example of server 102 is described with reference to FIG. 2.

In some embodiments server 102 stores animal data 110 in memory of server 102. In other embodiments, animal data 110 is stored remotely from server 102, but is accessible to server 102, such as across network 108 or another network. In some embodiments animal data 110 is stored in a database or other data record.

Animal data 110 includes information relating to a particular animal Examples of animal data include medical history data (including veterinarian notes, electronic medical records, immunization records, surgical history, medication records, medical treatment records, and identification of medical allergies), genealogy, owner information, owner's instructions in case of acute illness or injury (treat or put to sleep, who to contact if owner is unavailable), insurance information, and other data relating to the animal. In some embodiments, animal data is not considered or treated as confidential. However, in other embodiments, measures are taken to safeguard animal data 110 against unauthorized or improper use. For example, in some embodiments, communication of animal data 110 is performed in accordance with a secure data communication protocol, such as Secure Sockets Layer (SSL). Password protection is used in some embodiments. Other embodiments include other security features.

Records administrator system 104 is a computing system that operates to allow an administrator to oversee the administration of animal data 110 on server 102. In some embodiments, system 104 is the same as server 102, but typically system 104 is a separate computing system. Records administrator system 104 is typically operated by a person performing as a records administrator.

User computing device 106 is a computing system typically operated by veterinarians, animal health clinic, animal rescue, animal breeders (such as kennels), animal shelters, and animal's owner. In some embodiments user computing device 106 is a stationary device, such as at the owner's home or at the animal health clinic. However, in some embodiments, user computing device 106 is a mobile device, such as a laptop computer, cell phone, personal digital assistant, or other computing systems used by e.g. animal rescue teams and owner. In some embodiments user computing device 106 operates to communicate data across network 108, such as to access animal data 110.

In some embodiments animal identification device 112 is connected to user computing device 106 for identifying the animal. The animal health record associated with the identified animal is then obtained from server 102. Exemplary animal identification device 112 include biometric reader (such as retinal vascular pattern scanner, iris pattern recognition, or DNA reader) or a vitruvian image matching device for identifying muzzle prints. Other secondary identification methods may also be used, including reading implanted multifunction chips, interface for entering identification number from e.g. dog tag or earmark, pet identification card reader, and other devices for identifying an animal. In some embodiments multiple animal identification devices are used.

Figure 2:
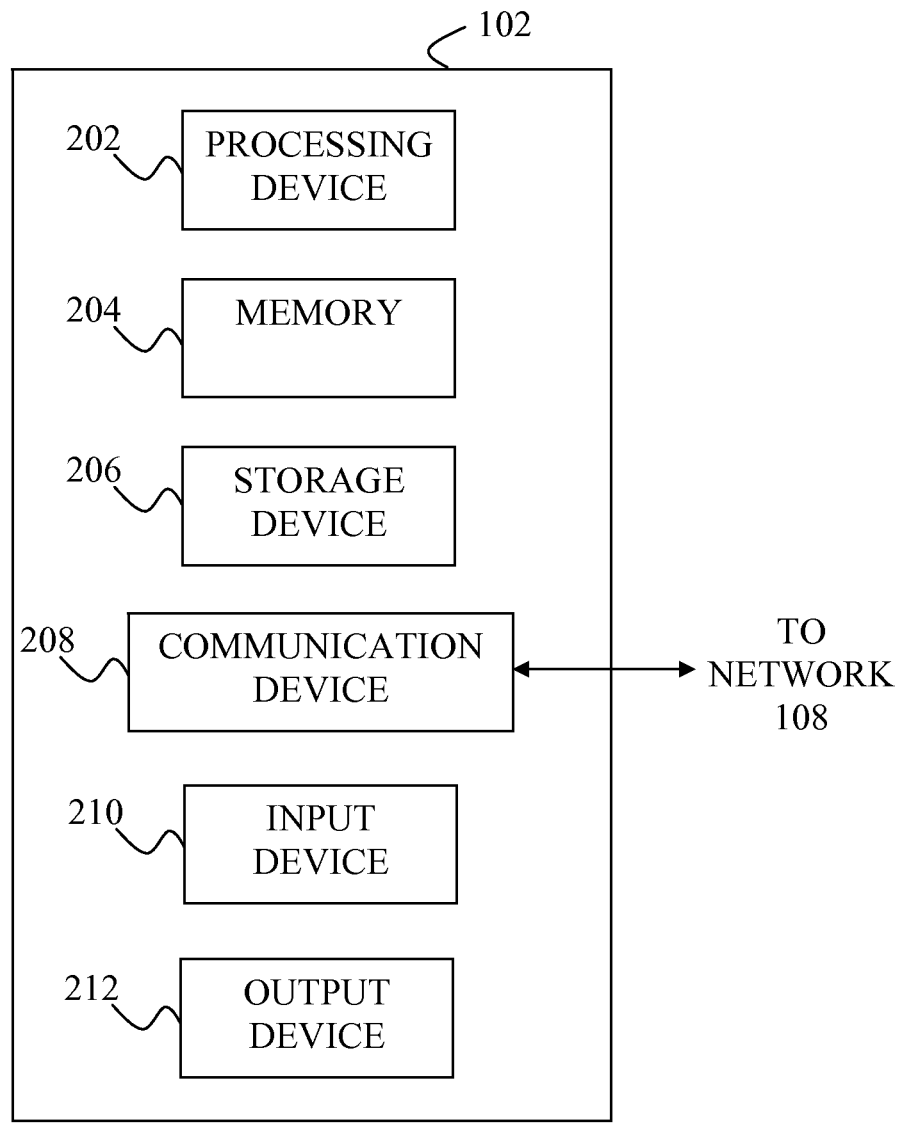
FIG. 2 is a schematic block diagram of an exemplary server of the data management system shown in FIG. 1.

FIG. 2 is a schematic block diagram of an exemplary server 102. Server 102 is a computing device that typically includes a processing device 202, memory 204, a storage device 206, a communication device 208, an input device 210, and an output device 212.

In its most basic configuration, server 102 typically includes processing device 202, memory 204, and communication device 208. Other embodiments include other components, such as illustrated in FIG. $2_1$ or yet other components.

Processing device 202 is a device that processes a set of instructions. One example of processing device 202 is a microprocessor. Alternatively, various other processing devices may also be used including central processing units ("CPUs), microcontrollers, programmable logic devices, field programmable gate arrays, digital signal processing ("DSP") devices, and the like. Processing devices may be of any general variety such as reduced instruction set computing (RISC) devices, complex instruction set computing devices ("CISC"), or specially designed processing devices such as an application-specific integrated circuit ("ASIC") device.

Examples of memory 204 include volatile (such as RAM), and non-volatile (such as ROM and flash) memory. In some embodiments, memory 204 is part of processing device 202, while in other embodiments memory 204 is separate from or in addition to that of processing device 202.

In some embodiments, server 102 also includes an additional storage device 206. Storage device 206 stores digital data. For example, some embodiments of server 102 include removable storage or non-removable storage, including, but not limited to, magnetic or optical disks or tape.

Computer storage media includes volatile and nonvolatile, removable and non-removable media implemented in any method or technology for storage of information such as computer readable instructions, data structures, program modules or other data. Memory 204 and storage device 206 are examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium that can be used to store the desired information and that can be accessed by server 102. Any such computer storage media may be part of server 102.

In some embodiments, memory 204 and/or storage device 206 store data instructions including one or more of an operating system, application programs, other program modules, and program data.

Server 102 also includes communication device 208 that allows server 102 to communicate with other devices, such as across network 108 (shown in FIG. 1). Communication device 208 is an example of communication media. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. Examples of communication media include wired media such as a wired network or direct-wired connection, and wireless media such as acoustic, radio frequency, infrared and other wireless media. The term computer readable media as used herein includes both storage media and communication media.

In some embodiments, server 102 includes one or more input devices 210, such as a keyboard, mouse, pen, voice input device, touch input device, or other input device. Some embodiments include one or more output devices 212₁ such as a display, speaker, printer, or other output device.

The computing system described above with reference to server 102 is also an example of other computing systems described herein. For example, in some embodiments records administrator computing system 104, and user computing device 106 are also computing systems as described above.

Figure 3:
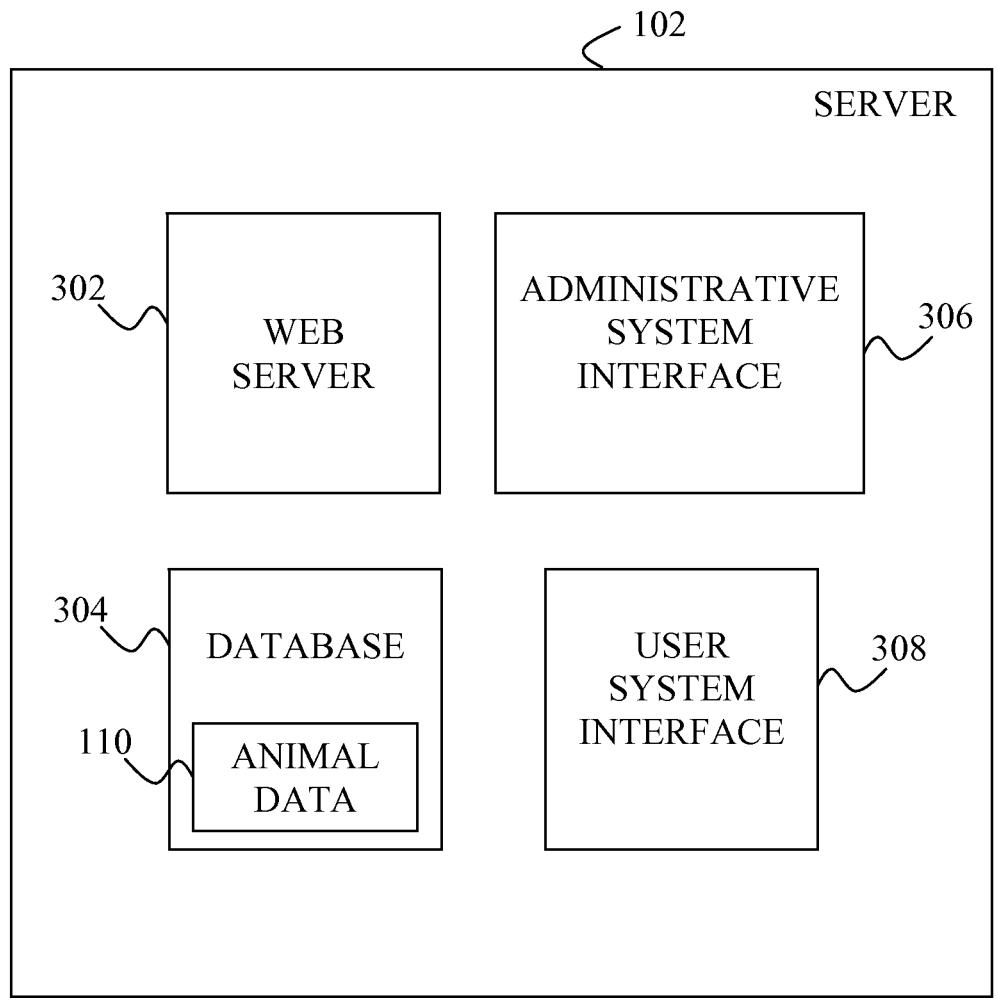
FIG. 3 is a functional block diagram of the server shown in FIG. 2.

FIG. 3 is a functional block diagram of an exemplary server 102. Server 102 includes Web server 302, database 304, administrative system interface 306₁ and user system interface 308. Other embodiments include more or fewer features, functions, or modules.

Web server 302 is a computer program that operates to communicate data defining one or more Web pages, such as across network 108 (shown in FIG. 1). Examples of Web server software applications include Internet Information Services from Microsoft Corporation and Apache HTTP Server. In some embodiments Web server operates to receive Hyper Text Transfer Protocol (HTTP) requests from clients (such as systems 104 or 106) and to serve HTTP responses along with data content, such as Web pages formatted in Hypertext Markup Language (HTML).

Database 304 stores animal data 110. Animal data 110 is typically associated with a single animal, such that database 304 includes a plurality of animal data records.

In some embodiments server 102 includes separate interface modules for communicating with particular groups of users. For example, server 102 includes administrative system interface 306 for communicating with an administrator (such as through records administrator system 104), and user system interface 308 for communicating with a user (such as through user computing device 106). It is sometimes desirable to provide separate interfaces for different groups of users, such as to provide different access rights to each group. For example, an animal owner using user computing device 106 is typically limited to accessing his or her own animal data 110, while a veterinarian using a user computing system such as system 106 will typically have access to the animal data of more than one animal. In some embodiments system interfaces 306 and 308 are custom software applications that control access rights and define particular Web pages to be displayed to the associated group. In some embodiments, system interfaces 306 and 308 also define one or more communication protocols and operate to communicate data according to the protocols. For example, in some embodiments some or all communication between server 102 and one or more groups of users occurs through one of system interfaces 306 and 308 rather than through Web server 302. In this way, data is communicated between the user system and server 102 according to a customized or other communication protocol.

Figure 4:
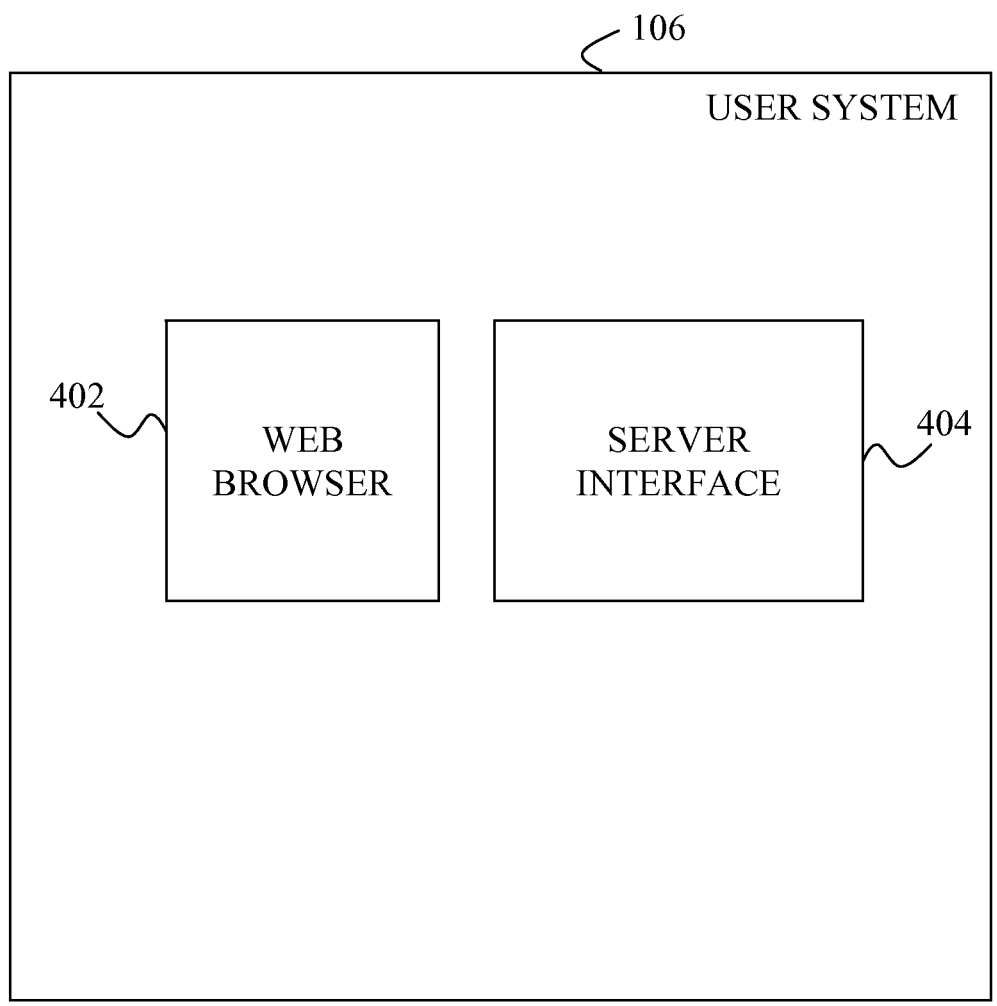
FIG. 4 is a functional block diagram of an exemplary user system of the animal data management system shown in FIG. 1.

FIG. 4 is a functional block diagram of an exemplary user computing device 106. User computing device 106 includes Web browser 402 and server interface 404.

Web browser 402 is a software application operating on user computing device 106 that operates to communicate with Web server 302 (shown in FIG. 3), such as to display Web pages from Web server 302. In some embodiments Web browser operates to send HTTP requests to Web server 302 and to receive HTTP responses along with data content from Web server 302. Examples of Web browser 402 include INTERNET EXPLORER® internet browser by Microsoft Corporation and the FIREFOX® Internet browser by the Mozilla Foundation.

In some embodiments user computing device 106 includes server interface 404 for communicating with user system interface 308 (shown in FIG. 3) of server 102. In some embodiments, server interface 404 is a custom software application that defines one or more communication protocols and operates to communicate data according to the protocols.

The system described above with reference to user computing device 106 is also an example of other systems described herein, such as records administrator system 104. In some embodiments these systems include additional modules.

Figure 5:
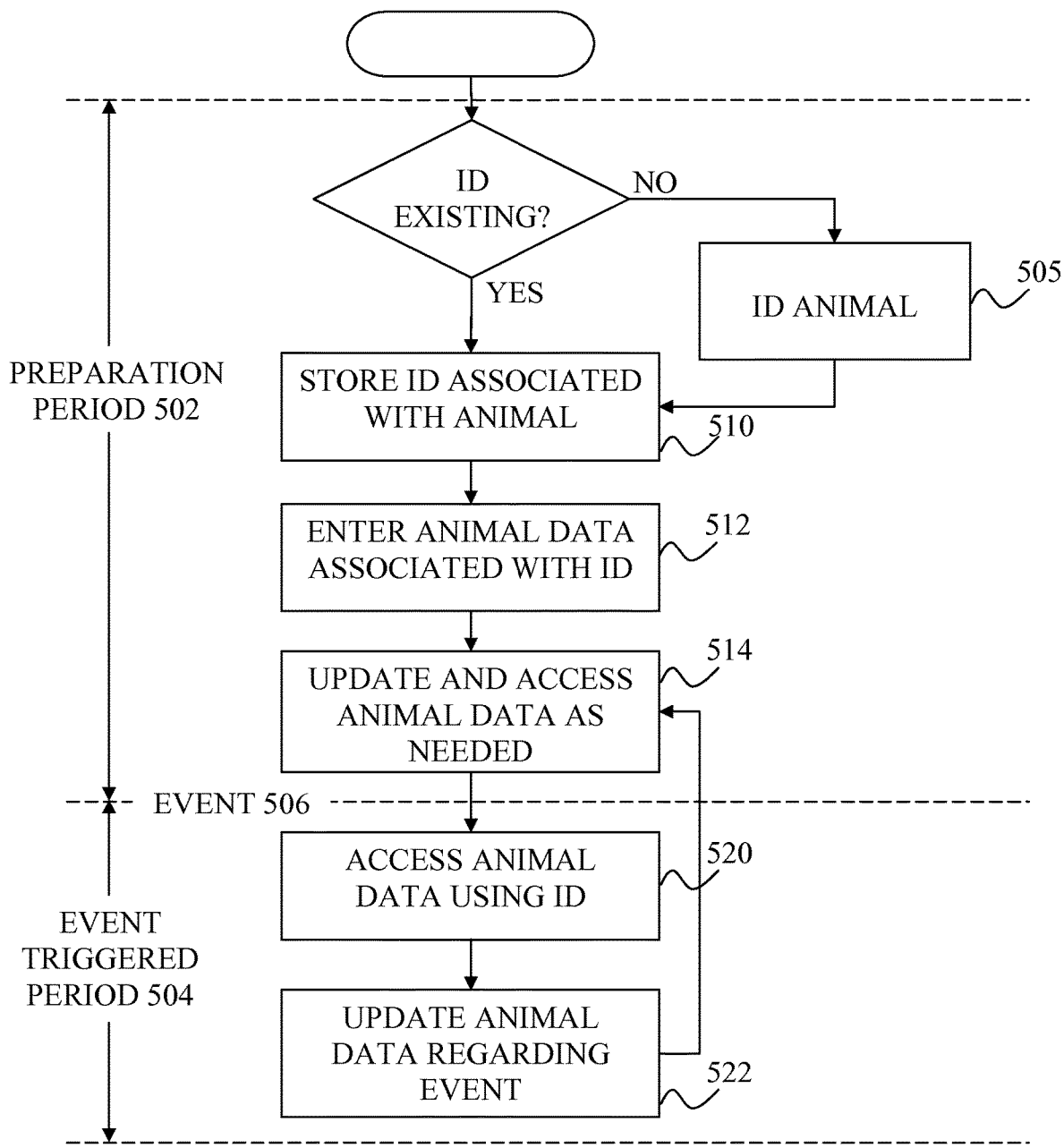
FIG. 5 is a flow chart illustrating an exemplary method of operating an animal data management system according to the present disclosure.

FIG. 5 is a flow chart illustrating an exemplary method 500 of operating an animal data management system. Method 500 includes two periods—a preparation period 502 and an event triggered period 504, which are separated by an event 506. Preparation period 502 includes operations 505, 510, 512, and 514. Event triggered period 504 includes operations 520 and 522.

When an animal already has an existing identifier such as an earmark or identification tag, preparation period 502 begins with operation 510 to store the identifier associated with that animal Else, when the animal does not have an existing identifier, an identifier is obtained for the animal in operation 505. In some embodiments operation 505 is a registration process. For example, a retina of an animal is scanned and a biometric or vitruvian identifier is generated based on unique retinal vascular patterns, shape of the iris, muzzle prints, etc. The biometric or vitruvian identifier is then stored in memory, such as on a server in operation 510. Other identifiers include RFID tag, implanted multifunction chip, identification number from e.g. dog tag, earmark, image of animal, DNA, and barcode from pet identification card. In some embodiment, an identifier (such as a biometric or vitruvian identifier) is given/registered to the animal although it already has an existing identifier.

Operation 512 is then performed to enter animal information associated with the identifier. For example, the owner's name and the animal's sex, weight, birth date, medical history data, genealogy etc. are stored in a database record associated with the identifier. in some embodiments, animal data 110 (shown in FIG. 1) is stored in the database and associated with the identifier. In some embodiments operation 512 is performed before operation 510.

After operations 510 and 512, operation 514 is performed to update and access animal information as needed. For example, a user accesses the animal info on server 102 through user computing device 106 (shown in FIG. 1). The user is allowed to edit and update some or all of the animal information as needed. The user also adds additional animal information in some embodiments.

Event 506 separates preparation period 502 from event triggered period 504. Event 506 is, for example, an event which causes a user to access animal data. Upon the occurrence of event 506, operation 520 is performed by a user to access animal data using the identifier. In some embodiments, operation 520 involves reading a biometric or vitruvian identifier from an animal, such as a retina vascular pattern or iris pattern image identification. The biometric or vitruvian identifier is matched with animal data associated with the biometric or vitruvian identifier. The user is then given access to the animal data associated with the animal. The animal data assists the user in providing proper action in response to the event.

In some embodiments, the event 506 is a lost or runaway animal A lost animal found by the non-owner could be admitted to e.g. a local shelter or an animal health clinic. A user in the shelter or the clinic uses the identifier to identify the animal and to access animal data 520 operation associated with the identifier. Thus, a lost animal is tracked and the owner is notified where to pick up his or her animal Many pet owners bring their pets while traveling or vacationing and it is common to use an animal collar including a GPS tracking device as identifier. Or, in some embodiments a multi function chip is implanted under the outer skin of the animal which has identification and GPS tracking capabilities. When the animal is provided with a GPS tracking device, the owner can track the animal using a mobile or stationary device.

Optionally, operation 522 is then performed to update animal data regarding the event. For example, a user at an animal shelter enters information about the event (such as where the animal was found), how the event was treated (such as calling the owner), and the results of the event (such as owner picked up animal). Any other information may be updated as desired during operation 522.

In some embodiments the event 506 is a found injured animal A user, such as a veterinarian, working in the animal health clinic or animal hospital, uses the identifier to get to the animal's health record in operation 520 and also to see the owner's statement or directive regarding treatment of the animal. In some embodiments, the lost animal is found by an animal rescue team, which can access animal data through a wireless communication device in the rescue vehicle using the identifier and find information about e.g. owner, medical history, immunizations, and how and if treating the animal. Examples of wireless communication devices include a radio transceiver, cell phone, wireless modem, satellite communication system, infrared communication system, and other communication systems that communicate using electromagnetic waves. An electronic animal record associated with an identifier of the animal, such as a biometric or vitruvian identifier, is helpful to verify that the animal has immunizations, especially rabies shots. Also, an electronic animal record makes it possible for the owner to speak for the animal, i.e. the owner's wishes regarding treatment. For example, the owner for various reasons may prefer not to treat a badly injured animal but instead put it to sleep. Such information would decrease the suffering of the injured animal and also save the owner the cost for treatment he or she did not want for the animal. The owner may also store an advanced directive or living will for the animal. Such advanced directives might be the owners wish to donate organs of a diseased animal to e.g. universities for study. Or, the wishes of the owner regarding what to do with and where to place the animal if the owner dies or something else happens that makes it impossible for the owner to take care of the animal.

Optionally, operation 522 is then performed to update animal data regarding the event. For example, a user at an animal health clinic enters information about the event (such as a description of a medical condition of the animal or a diagnostic test that was performed), how the event was treated (such as prescribing a medication or doing surgery), and the results of the event (such as that the medication took away the symptoms or the animal was put to sleep).

In some embodiment the event 506 is an acute illness of an animal being brought to an animal hospital or clinic which is not the usual hospital or clinic. It is more and more common to bring pets when traveling or going on vacation. Most pet owners do not bring their pet's medical records since these papers usually are not considered necessary for traveling. When the pet has an electronic record associated with an identifier, it is easy to get proper medical attention without delay by any animal hospital in case of a medical emergency. The user of such hospital or clinic simply access animal data in operation 520 and gets the animal's health or medical records. In some embodiments, animal health care costs are reduced because veterinarians are able to provide proper health care and do not perform unnecessary testing or treatment. For example, if a test has already been performed, information about the results of the test is available to the veterinarian such that retesting may not be necessary. Similarly, if a therapy has already been provided (or tests have already confirmed that therapy is not necessary), the veterinarian is provided with this information so that the veterinarian does not unnecessarily provide the therapy. For example, if an animal has already been immunized against a condition, such as rabies, the veterinarian is provided with that information to prevent the veterinarian from re-immunizing the animal. Animal health care costs are reduced in some embodiments by preventing improper treatment. For example, if an animal is allergic to a particular drug, allergy information is provided to the veterinarian so that the veterinarian does not administer that drug. Optionally, operation 522 is then performed to update animal data regarding the event.

In some embodiments the event 506 is finding a dead or dying diseased animal Accessing animal data using the animal's identifier in operation 520 could help to track where and from what animals are getting sick and also what animals.

In some embodiments the event 506 is sale of an animal Since animal data is tied to the animal and independent from the owner, it is easy to transfer medical records to a new owner. Also, by accessing animal data using the animal's identifier in operation 520, it is possible to identify where the animal has come from, to identify previous owners, and also to issue certificate regarding animal genealogy. For example by using a biometric or vitruvian identifier, it is possible to ascertain that e.g. a horse is a claimed horse having a certain bloodline.

Figure 9:
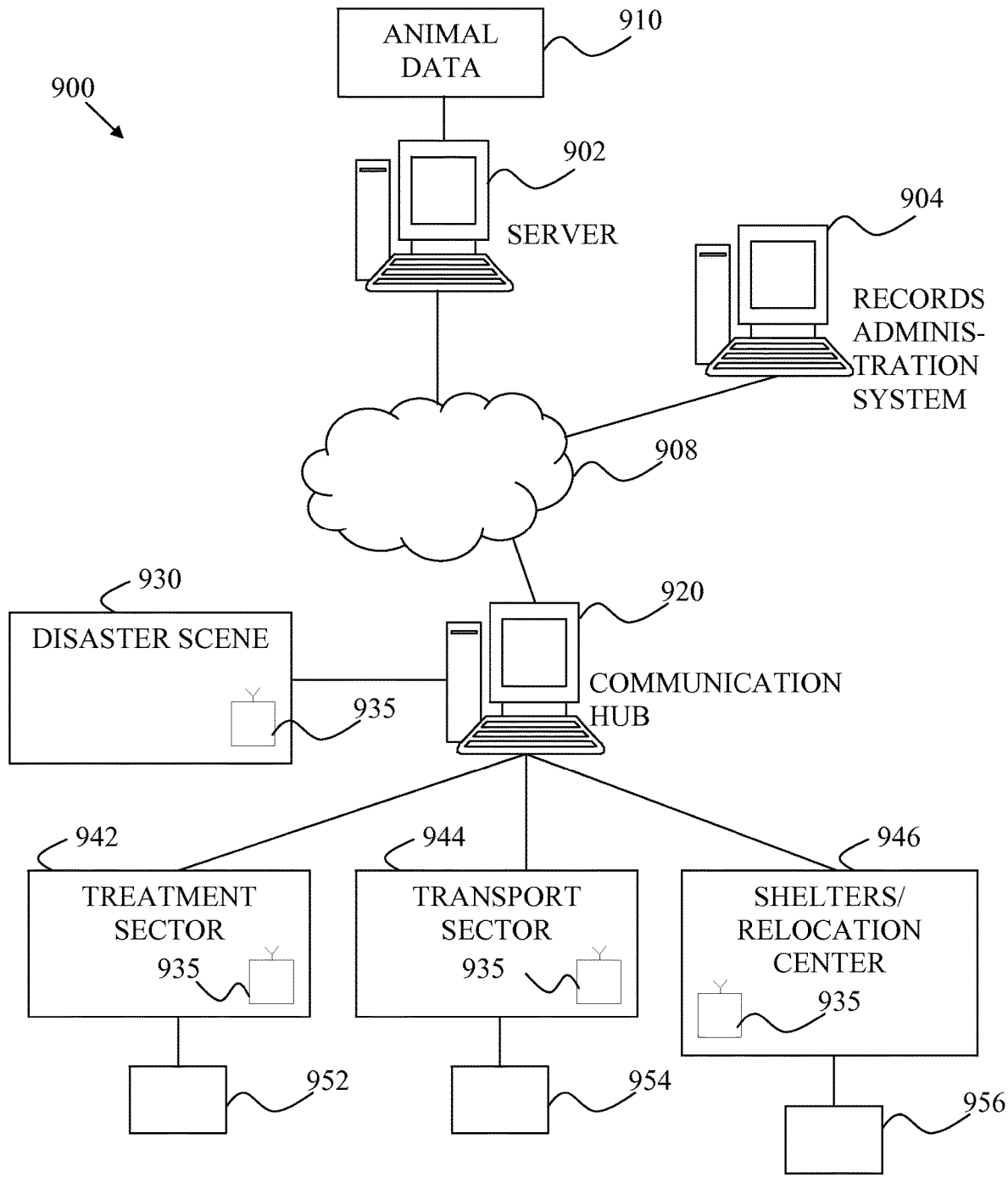
FIG. 9 is a schematic block diagram of an exemplary disaster response system according to the present disclosure.

In some embodiments the event 506 is a striking disaster, such as earth quakes, avalanches, flooding, and other natural disasters but also car or bus accidents etc. It is common to use search and rescue dogs in certain types of disasters such as earth quakes to find and rescue buried people. A user accessing animal data in operation 520 may use the system to track rescue dogs. Also, search and rescue animals need to be certified and need to have updated health records available at all times. Such documents will be available when accessing animal data in operation 520. A disaster response system is shown in FIG. 9 and further discussed below in conjunction with FIG. 9.

In some embodiments, the event 506 is crossing a U.S. state line with a horse or other equine species. To legally cross state lines with a horse, there are legal documents that need to be acquired and kept while crossing state lines. State-level administrative agencies or departments have specific requirements about which documents need to be maintained for transport of a horse across state lines. One document needed is a proof of a current negative Coggins test for Equine Infectious Anemia. Also, a health certificate issued within 30 days prior to crossing state lines is needed. A health certificate is simply a form with the starting point and destination filled in, with the signature of a veterinarian confirming the horse described in the record/paperwork is free of any infectious diseases. Thus, using an identifier for each horse, such as a biometric or vitruvian identifier, associated with an electronic horse record simplifies traveling between states since it is no longer necessary to bring paperwork. All necessary information and documentation is found in the horse's electronic record.

Optionally, operation 522 is performed after crossing a state line to update animal data regarding the event to be able to track where in which states a certain horse has been to.

In some embodiments, operation 522 involves billing of e.g. medical expenses incurred. In some embodiments, users at animal health clinics provide invoices such as by sending the invoices to server 102, shown in FIG. 1. In some embodiments, invoices are then electronically delivered to the owner of the animal such as through user computing device 106, shown in FIG. 1. In some embodiments billing is performed more quickly. In some embodiments, records of invoices and associated payments (by animal's owner) are stored with the animal's records.

In some embodiments operation 522 also involves medical transcription. For example, a user at an animal health clinic records dictation of medical care or diagnosis that was performed, such as in a digital audio file. The digital audio file is then transferred to server e.g., server 102, shown in FIG. 1. In some embodiments, the server transfers the file to a medical transcription service that converts the dictation into a medical record. The medical record is then transferred back to the server and stored in the animal's records. In some embodiments the audio file is also or alternatively stored in the animal's records.

Event triggered period 504 is then concluded, such that method 500 returns to operation 514 of preparation period 502, where animal data is updated or accessed as needed.

Example embodiments will now be described with reference to exemplary graphical user interfaces. In some embodiments the graphical user interfaces are defined by Web pages that are hosted on a server 102 of system 100. Users can access these pages using a Web browser.

Figure 6:
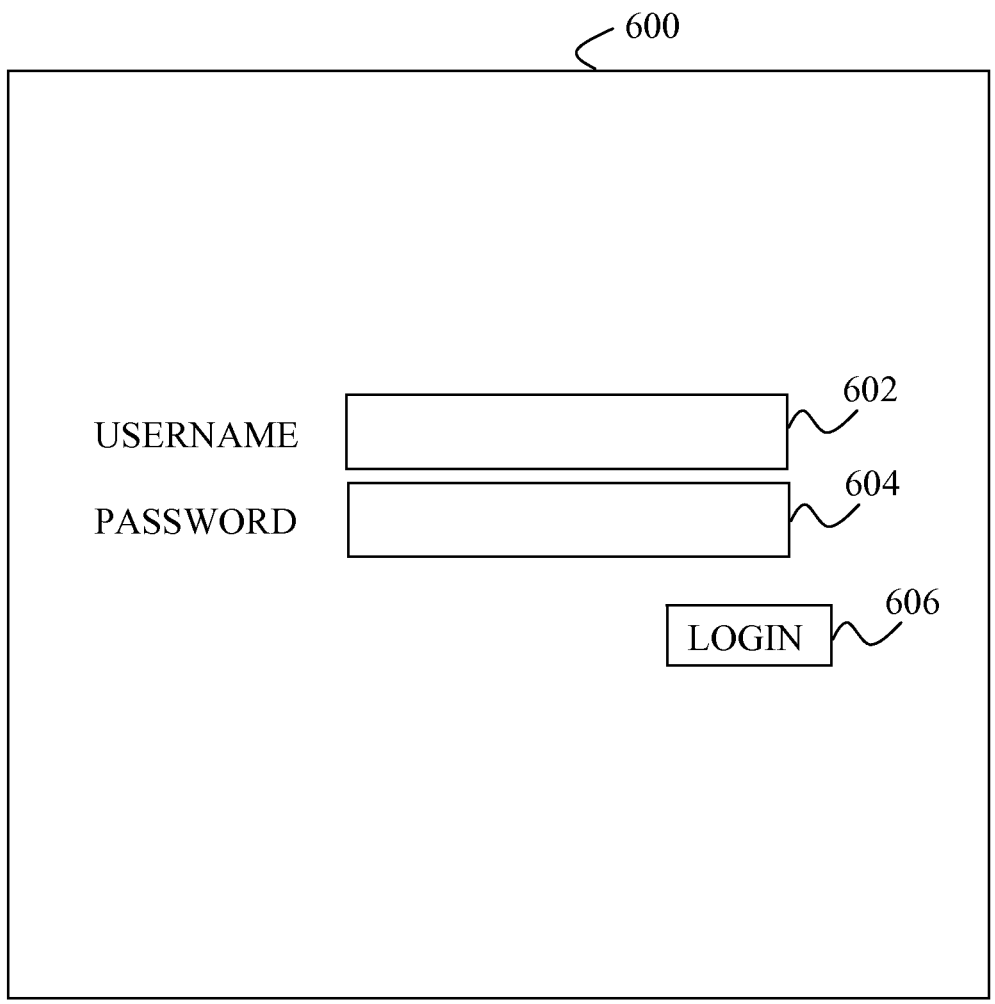
FIG. 6 is an exemplary login interface according to the present disclosure.

FIG. 6 is an example of a screen comprising an exemplary login interface 600. Login interface 600 includes username prompt 602, password prompt 604, and login button 606.

In some embodiments a graphical user interface begins with login interface 600. In some embodiments, login interface is defined by server 102 and is displayed by a computing system, such as user computing device 106 (or another computing system including records administrator system 104), shown in FIG. 1.

Login interface 600 prompts a user to enter a username and a password in order to proceed. Username prompt 602 prompts the user for a username and password prompt 604 prompts the user for a password.

After the username and password have been entered by a user, the user then selects login button 606. In some embodiments, upon selection of login button 606 the username and password are communicated to a server for evaluation. If the username and password match a username and password for an active user account, the user is allowed to gain access into the system. For example, a home interface is next displayed in some embodiments, such as shown in FIG. 7.

In some embodiments a user account is associated with a role. Examples of user roles include an animal owner role, an administrator role (such in an animal shelter, kennel or an animal health clinic), and a veterinarian role. The role associated with a user account defines the access rights and permissions available to that set of users. In some embodiments different user interface displays are displayed to different users according to the associated user role.

Figure 7:
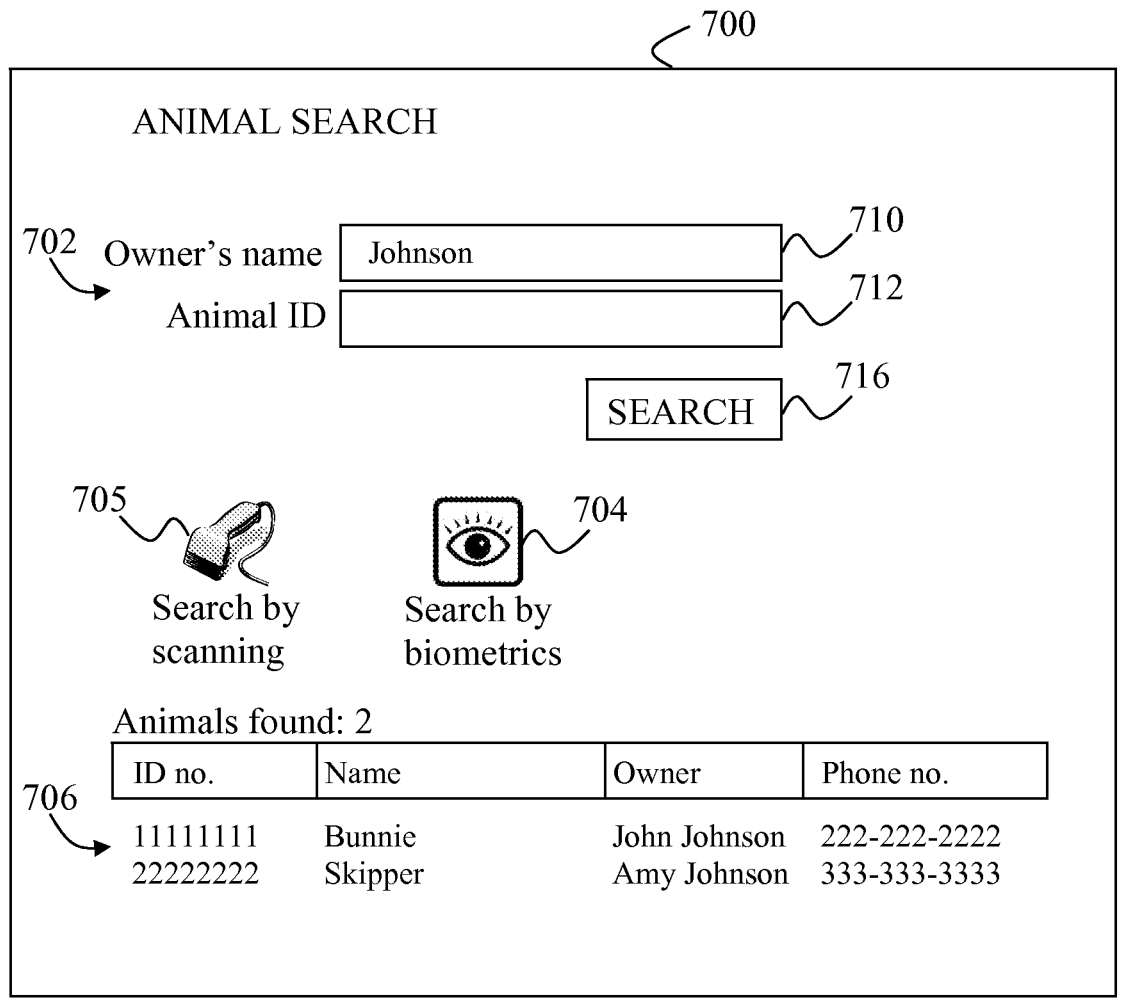
FIG. 7 is an exemplary search interface according to the present disclosure.

FIG. 7 is an example of a screen comprising an exemplary animal search interface 700. The animal search interface allows a search to be performed to locate animal records matching search criteria Animal search interface 700 includes search fields 702, search by biometrics selectable control 704, search by scanning selectable control 705, and search results 706. Selectable controls 704 and 705 may be any type of selectable user interface, such as button, check box, link or the like.

Search fields 702 include owner's name prompt 710, animal ID prompt 712, and selectable control 716 for search, for example. Owner's name prompt 710 is a field where a user enters a last name, part of a last name, or a first and a last name to be searched Animal ID prompt 712 is a field where a user enters an animal identification number or part of the identification number to be searched, such as from an earmark or from a tax tag. A user can enter search criteria into one or more of the search fields 702 and then click search control 716 to search the animal records. The search criteria are then used by the server to search through the animal records to find those records that match the search criteria. The results are displayed in search results 706.

Search by biometrics selectable control 704 is selected by a user to initiate a search by a biometric or vitruvian identifier, such as a retina reader. Upon selection of search by biometrics selectable control 704, a biometric reader is activated to read the biometric or vitruvian identifier. When the biometric or vitruvian identifier is received, the server uses the identifier to search for the matching animal record.

Search by scanning selectable control 705 is selected by a user to initiate a search by an identifier, such as a barcode reader, a reader reading an implanted chip, and a reader reading a RFID tag. Upon selection of search by scanning selectable control 705, a reader is activated to read the identifier. When the identifier is received, the server uses the identifier to search for the matching animal record.

After a search has been performed based on the search criteria provided in search fields or based on the biometric or the scanned identifier of the animal, the search results 706 are displayed. In the illustrated example, a search has been performed for and animals having an owner with a last name beginning with "Johnson". Two matching animals are listed, including Bunnie and Skipper. The animal name, the ID no. or the owner name of each matching record is a hyperliuk that can be selected by a user to bring the user to the animal profile interface associated with the animal.

Figure 8:
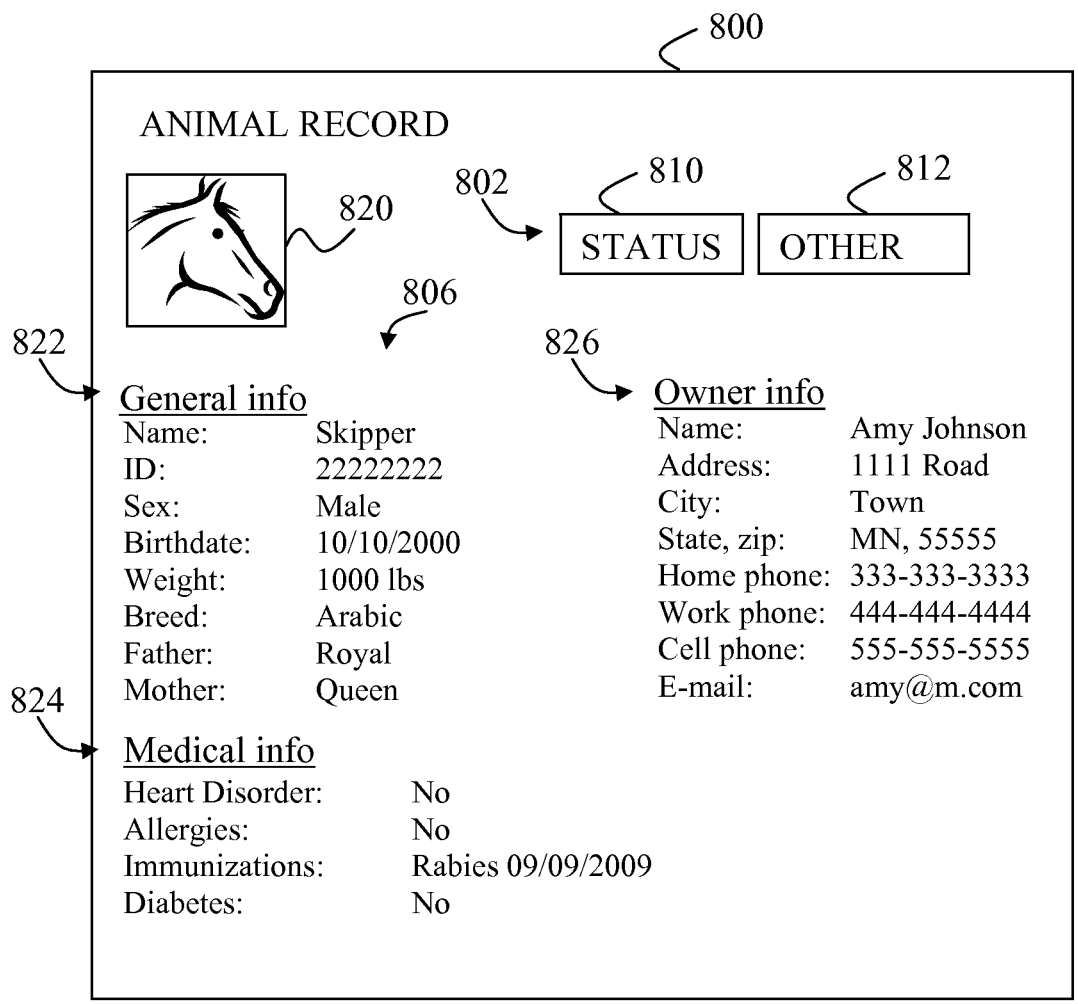
FIG. 8 is an exemplary record interface according to the present disclosure.

FIG. 8 is an example of a screen comprising an exemplary animal profile interface 800. Animal profile interface 800 includes navigation controls 802 and animal profile 806. Navigation controls 802 include in this example Go To Status button 810, and Other button 812. Animal profile 806 includes photo section 820, general info section 822, medical info section 824, and owner info section 826.

Animal profile interface 800 is an interface that provides information regarding a particular animal. In some embodiments the information includes data from animal data 110, shown in FIG. 1.

Navigation controls 802 are selectable by a user to jump to a different interface display. When a user selects Go To Status button 810, an animal status interface is displayed that is associated with the currently identified animal Other button 812 illustrates in this example for simplicity a number of different navigation controls that may be used to jump to another interface display, such as medical history of the animal, detailed genealogy, issued certificates, insurance, emergency contact, wishes, etc. In some embodiments an additional navigation control is an owner button, which when selected jumps to the health care record of the owner and, thus, a link between the animal's record and the owner's record is created. This is useful in the event of a pet found next to an injured person who cannot speak for himself or herself. In some embodiments an additional navigation control is associated with an advance directive living will for the animal, which when selected jumps to another interface display showing the will of the owner regarding the animal, such as a wish to donate the animal's organ to universities for study and information of where to place or what to do with an animal if the owner dies or cannot take care of the animal anymore.

Animal profile 806 displays information about an animal. In some embodiments, animal profile 806 includes multiple sections, including photo section 820, general info section 822, medical info section 824, and owner info section 826. Some embodiments include additional sections not visible in FIG. 8, such as other wishes section, emergency contact information section, primary veterinarian section, health insurance section, and detailed status section.

Photo section 820 includes a photograph of the animal, if available. If no photo is available for a particular animal an image is displayed that so indicates. General info section 822 displays general information about the animal Examples of general information include name, ID number, gender, date of birth, weight, breed and genealogy.

Medical info section 824 includes information regarding medical conditions of the animal Examples of medical conditions that are displayed in medical info section 824 include different disorders, allergies, info about immunizations, diabetes, and any other medical info of interest such as current medication. In some embodiments, medical info are associated with a YES or NO field that indicates whether or not the animal currently has or previously has had the condition, and includes a note field where further details regarding the condition are displayed.

Owner info section 826 includes information regarding the owner of the animal Examples of owner info include name, address, home phone number, work phone number, cell phone number, mail address and, if the owner has a location-transmitting device, such as a GPS-enabled smartphone, the owner's present location.

In some embodiments, all or some of the information in animal profile 806 is hyperlinked to access more details of the specific information.

Another possible section is an Other Wishes section. In some embodiments the Other Wishes section is a text box that displays any other wishes that an animal owner would like made known to a caregiver/veterinary during a health event.

Another possible section is an Emergency Contact Information section. This section displays information identifying who should be contacted upon an emergency if the owner cannot be reached. Examples of emergency contact information contained in this section include the contact information for one or more emergency contacts. For each contact, contact information includes contacts name, home telephone number, work telephone number, and cell phone number.

In some embodiments, the Emergency Contact Information section includes an automatic notification option. For example, each emergency contact includes an option for automatic emergency notification. If automatic emergency notification is selected, the system will automatically contact the person in the manner indicated upon the occurrence of a health event, such as an injured animal. In one embodiment, a health event is deemed to have occurred whenever a caregiver such as a veterinarian or an animal rescue team (using a user computing system) enters the animal's biometric or vitruvian identifier, such as by scanning the animal's retina with the computing system. Once the system determines that a health event has occurred, the emergency contact(s) that have the automatic emergency notification feature enabled will be notified that a health event has occurred. Such notification can include an e-mail message, a text message, a telephone call with a voice message, a facsimile, or any other suitable communication. In some embodiments the notification is only a notification that a health event has occurred to the animal. In other embodiments, additional information is provided, such as the name and address of the animal health clinic facility that the animal is going to or being treated at, a description of the health event, a contact telephone number or web address where the emergency contact can get more information about the health event, or other information. In some embodiments, the emergency contact can access an emergency contact interface Web page that provides further information.

Another possible section is a Primary Veterinary Care section. The Primary Veterinary Care section displays information about the primary veterinarian. Examples of information about the primary veterinarian include the veterinarian's name, direct telephone number, facility name, and facility telephone number.

Another possible section is a Health Insurance section that displays information about the owner's health care coverage for the animal Examples of health care information include provider name, provider telephone number, name of policy holder, and policy number.

Another possible section is a Special Care Instructions section that displays information regarding the owner's desires for care upon the occurrence of a health event. In one example, Special Care Instructions includes a list of possible special care instructions associated with a YES or a NO. A YES indicates that the owner does want the caregiver to follow the associated Special Care Instruction and NO indicates that the owner does not want the caregiver to follow the associated Special Care Instruction. Examples of Special Care Instructions include: do not x-ray, medication for pain only, medication/treatment/hospitalization as needed, and euthanize if badly injured.

In some embodiments, animal profile interface 800 is not only a display that provides information about an animal, but also receives information from a user to update the animal's profile. For example, the owner logs into the system through user computing device 106 (shown in FIG. 1) and accesses animal profile interface 800. The owner then enters or edits the information as needed. Alternatively, data may only be edited by an administrator in some embodiments. For example, an owner communicates with the administrator and the administrator makes changes to the animal profile as needed. A benefit of this is that the administrator can act to ensure that information is not improperly changed for added security. In some embodiments a user in an animal hospital/health clinic, a kennel, or a shelter is allowed to edit and modify information in the animal profile.

More or less information is included in animal profile interface 800 in some embodiments.

FIG. 9 is schematic block diagram of an exemplary disaster response system 900. System 900 includes server 902, records administrator computing system 904, communication hub 920, disaster scene system 930, treatment sector 942, transport sector 944, and shelter/relocation center sector 946. In some embodiments communication occurs across network 908. Server 902 includes animal data 910. Biometric readers 952, 954, and 956 are coupled to treatment sector 942, transport sector 944, and shelter/relocation center sector 946 respectively. In some embodiments, biometric readers are also coupled to the disaster scene 930.

Briefly, some embodiments of disaster response system 900 operate to provide quick and convenient access to animal data 910, while protecting the privacy of animal data 910 from unauthorized access. For example, health records and information of an animal are stored in animal data 910 of server 902. The disaster response system may be used and set up by local agencies, such as EMA (Emergency Medical Associate), state agencies, such as EOCs (Emergency Operations Centers), and federal emergency management agencies (FEMA, such as FOC (FEMA Operations Center) or DFO (Disaster Field Offices).

Server 902 is a computing system that stores or is able to access animal data 910. Server 902 is in data communication with network 908. In some embodiments server 902 is a Web server that generates data for one or more web pages. The data is communicated across network 908 to a computing system operating a browser software application.

In some embodiments server 902 stores animal data 910 in memory of server 902. In other embodiments, animal data 910 is stored remotely from server 902, but is accessible to server 902, such as across network 908 or another network. In some embodiments animal data 910 is stored in a database or other data record.

Animal data 910 includes information relating to a particular animal Examples of animal data include medical history data (including veterinarian notes, electronic medical records, immunization records, surgical history, medication records, medical treatment records, and identification of medical allergies), genealogy, owner information, owner's instructions in case of acute illness or injury (treat or put to sleep, who to contact if owner is unavailable), insurance information, and other data relating to the animal. In some embodiments, animal data is not considered or treated as confidential. However, in other embodiments, measures are taken to safeguard animal data 910 against unauthorized or improper use. For example, in some embodiments, communication of animal data 910 is performed in accordance with a secure data communication protocol, such as Secure Sockets Layer (SSL). Password protection is used in some embodiments. Other embodiments include other security features.

Records administrator system 904 is a computing system that operates to allow an administrator to oversee the administration of animal data 910 on server 902. In some embodiments, system 904 is the same as server 902, but typically system 904 is a separate computing system. Records administrator system 904 is typically operated by a person performing as a records administrator.

Upon occurrence of a disaster, such as a natural disaster, a man-made disaster, and pandemics, emergency response teams immediately set up communication hub 920 for establishing an infrastructure coordinating efforts between different emergency response functions, such as first responders at the scene of disaster 930, treatment sector 942, transport sector 944 and temporary shelters/relocation centers 946. Internet connectivity is maintained utilizing communication means, such as radio and satellite. Temporary communication towers can be erected to provide wireless communication capability. All those responding to the disaster can be equipped with mobile computing devices 935 providing access to server 902.

Communication hub 920 provides access to server 902 via network 908. The size and functionality of communication hub 920 is triggered by the size and severity of the disaster. Communication hub 920 may be access point to a wide area network (WAN), such as the internet, and to local area networks (LAN).

Treatment sector 942 includes existing animal hospitals and temporary triage tents where emergency care is provided. Biometric readers 952 are used to read a biometric or vitruvian identifier of found animals. If the found animals are already registered in server 902, their biometric or vitruvian identifier can provide immediate access to crucial health information stored in animal data 910. If the animals are not registered, emergency response teams at treatment sector 942 or at disaster scene 930 can register those animals, including identifying their current location. As a result, the emergency response teams at treatment sector 942 are able to positively identify the animal and review the health records of the animal immediately (in "real-time") to assist them in providing proper medical care to the animal. Similarly, when the animal enters the hospital, the biometric or vitruvian identifier of the animal is read with biometric reader 952 to provide access to the animal's information and medical records.

An example of a biometric reader is a charge coupled device (CCD) for obtaining a digital image of an eye. Other biometric readers are used in other embodiments, such as laser, blood analyzer, pulse detector, or keystroke recognition system. In some embodiments multiple biometric readers are used.

Rather than, or in addition to, using a biometric reader, some embodiments include an alternate animal identifier. An example of an animal identifier is an RFTD tag, and the like.

Transportation sector 944 is associated with emergency vehicles, such as ambulances and helicopters. In some embodiments transportation sector 944 communicates wirelessly with communication hub 920 and/or with network 908 with mobile computing devices 935. Examples of mobile computing devices 935 include a laptop computer, a handheld computing system, a tablet computer, a personal digital assistant (PDA), a cell phone, and other computing systems.

Examples of wireless communication devices include a radio transceiver, cell phone, wireless modem, satellite communication system, infrared communication system, and other communication systems that communicate using electromagnetic waves. Typically, health care is provided by the emergency vehicles, such as an EMT. Transportation sector 944 access animal data 910 from server 902 in some embodiments.

In some embodiments, transportation sector 944 includes biometric readers 954. The biometric readers 954 are configured to read a biometric or vitruvian identifier of an animal and are similar to biometric reader 952 discussed above.

Shelters or relocation centers 946 are established for people and animals that have been displayed by the disaster. At these temporary shelters mobile computing devices 935 are used to update data in server 902, including any important health care information and location of the victims and animals. For simplicity, the shelters or relocation centers 946 are illustrated as one unit, while in reality separate shelters and relocation centers are usually set up for people and animals. The pet separated from the owner may end up in a shelter in one town, and the owner may end up in another town. A user at, for example, the shelter or relocation centers 946 accessing animal data 910, can use the system to find the owners to a found animal. Or, the owner can access animal data 910 and find out where the pet currently is sheltered. Each person and animal at shelters or relocation centers 946 is registered into server 902 (if they are not already registered), the animal in animal data 910 and the person in a user data (not shown in FIG. 9) connected to server 902, and the location of each person and animal is identified as being at the particular shelter or relocation center (or at a particular hospital, etc.). If the animal is moved to a different shelter, the animal data 910 is updated accordingly.

In some embodiments, shelters or relocation centers 946 include biometric readers 956. The biometric readers 956 are configured to read a biometric or vitruvian identifier of an animal and are similar to biometric reader 952 discussed above.

Mobile computing devices 935 include a laptop computer, cell phone, personal digital assistant, or other computing systems. In some embodiments shelters or relocation centers 946 operate to communicate data across network 908, such as to access animal data 910.

Disability assistant animals, such as dogs, that are separated from the person with a certain disability during a disaster may be found and reunited with its owner using the system. It is expensive to train animals to assist persons with disabilities, so it will save a lot of money to be able to reunite a trained animal to its owner, not to mention the relief it will be for the disabled person to get his or her animal back. Furthermore, a pet such as a dog is likely to stay by its owner that might be injured, and by accessing animal data using the dog's identifier information about its owner may be obtained. In some embodiment animal data is linked to the owner's health care data records. Since the probability that an injured person next to a dog is the dog's owner is high, identification of that person may be made by identifying the dog. And, also fast access to the injured person's medical records may be made. However, it needs to be verified that the injured person really is the owner of the dog before any medical treatment is started.

Figure 10:
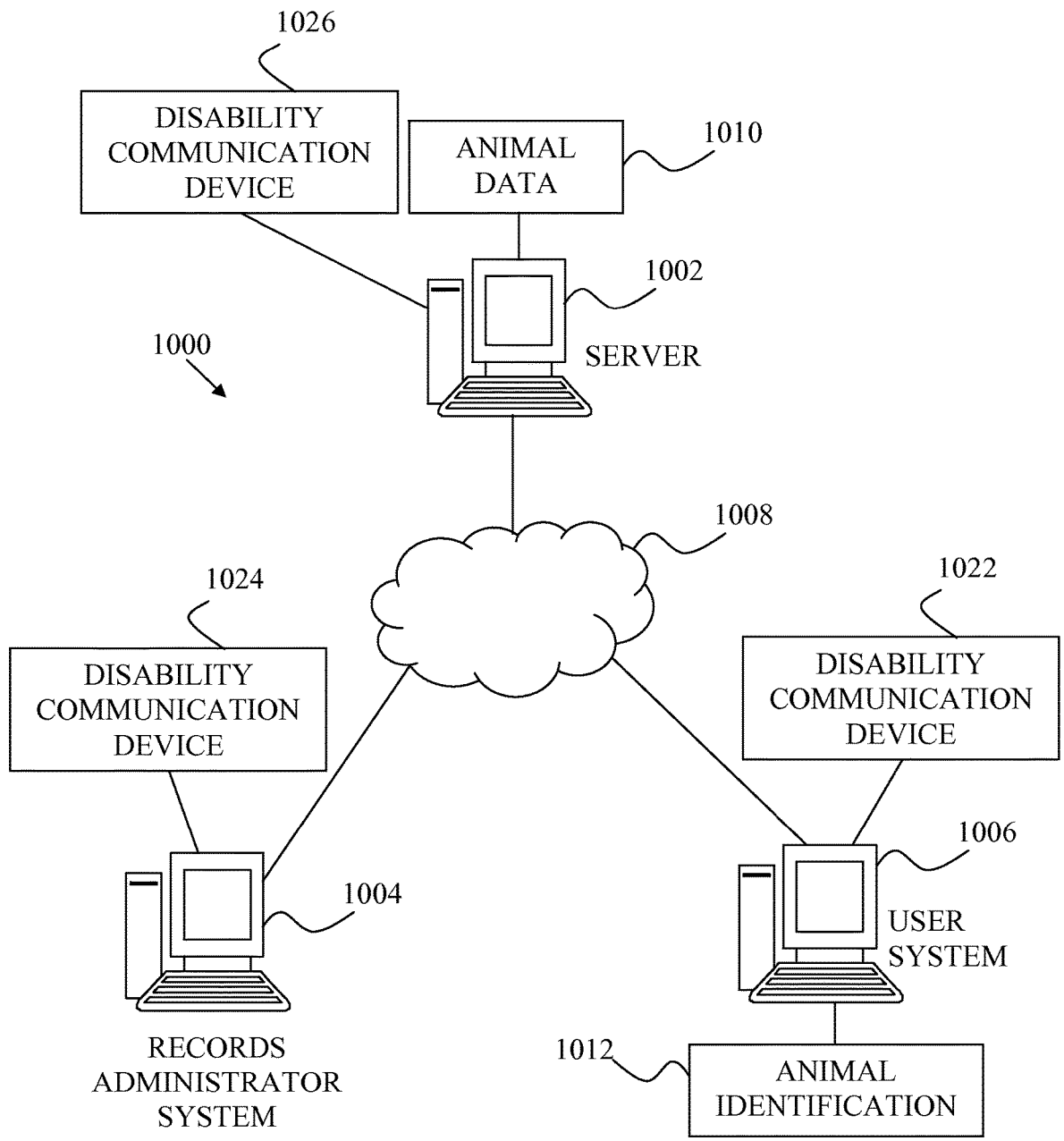
FIG. 10 is a schematic block diagram of another exemplary animal data management system according to the present disclosure.

FIG. 10 is a schematic block diagram of another exemplary animal data management system 1000. The system 1000 includes server 1002, records administrator computing system 1004, and user computing device 1006. In some embodiments communication occurs across network 1008. Server 1002 includes animal data 1010. An animal identification device 1012 is coupled to user computing device 1006. These elements of the system function similarly to the corresponding elements of the system shown in FIG. 1 and is not further described herein.

The system 1000 further includes first and second communication devices 1022, 1024 and 1026 for people with special needs. The first disability communication device 1022 is connected to the user system 1006 to aid a person with a disability. The second disability communication device 1024 is connected to the records administration system 1004 to allow the administrator to communicate with the person with the disability. The third disability communication device 1026 is connected to the server 1002. Examples of communication devices used are Video Remote Interpreting (VRI) devices and Text Telephone (TTY) devices. VRI devices aid people who are deaf and are videoconferencing equipment to connect the person with the disability to an interpreter (of sign language) in a remote location over the internet. TTY devices are a special device that lets people who are deaf, hard of hearing, or speech-impaired use the telephone to communicate, by allowing them to type messages back and forth to one another instead of talking and listening. In the system 1000 shown in FIG. 10, the second communication device 1024 is directly connected to the records administration system 1004 and the third disability communication device is directly connected to the server 1002. However, in other embodiments the second and third communication devices are remotely connected to the records administration system 1004 and the server 1002, respectively, over the network 1008. Other known communication devices for aiding persons with disabilities may also be used, such as voice communication devices for blind people.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims.

What is claimed is:

1. An animal data management system comprising:
  a server for registering an animal by receiving animal data and animal identification information comprising:
    a first biometric identifier selected from a group consisting of: Iris patterns; retinal vascular patterns; or DNA; or a vitruvian identifier selected from a group consisting of: muzzle prints;
  a memory configured to store the animal data and animal identification information including the first biometric or vitruvian identifier;
  a database for storing animal identification data, animal health care information, and owner information associated with the animal identifier information;
  a processor device and at least one computer storage medium, the at least one computer storage medium storing data instructions, wherein the data instructions are executable by the processor device to:
    receive the animal identifier information of an animal and store the animal identifier information in the database;
    receive animal health care information related to the animal's health and owner information related to an owner of the animal corresponding to the animal identifier information; and store the animal health care information and the owner information in the database with the corresponding animal identifier information, wherein at least one of the animal health care information includes a veterinarian procedure performed on the animal to treat or diagnose the animal and the owner information includes at least one of the owner's health directive for the animal to inform a third party of the owner's wishes or the owner information includes the owner's statement for treatment of the animal to inform the third party of the owner's wishes;

a user system for accessing the animal data from the memory, wherein the animal data includes a health certificate with the signature of a veterinarian confirming the animal is free of an infectious disease; and an interface for receiving a request for information, the request for information including the animal identifier information, and for providing a response to the request for information, the response to the request for information including the animal healthcare information and the owner information corresponding to the animal identifier information in the database.

2. The animal data management system of claim 1, wherein the animal health care information includes a status of the animal.

3. The animal data management system of claim 1, wherein the data instructions are further executable by the processor device to:

transmit at least a portion of the status to the owner of the animal in response to the receipt of the animal identifier information based on the owner's information.

4. The animal data management system of claim 2, wherein the status of the animal includes a location of the animal, thereby allowing the owner to retrieve the animal.

5. The animal data management system of claim 1 wherein the status includes at least one of whether the animal was put to sleep, whether the owner was contacted, whether the owner picked up the animal, a location of the animal, or state lines crossed by the animal.

6. The animal data management system of claim 3, wherein the data instructions are further executable by the processor device to transmit at least a portion of the animal health care information to a third party.

7. The animal data management system of claim 6, wherein the data instructions are further executable by the processor device to update the animal health care information with at least one of a veterinarian procedure performed on the animal to treat or diagnose the animal or a status of the animal.

8. The animal data management system of claim 2, wherein at least one of the owner's health directive or statement for treatment of the animal include an indication of at least one of do not x-ray the animal, medication for pain only, medication as needed, treatment as needed, hospitalization as needed, or euthanize when badly injured.

9. The animal data management system of claim 1, wherein the owner information includes the owner's health insurance information for the animal.

10. The animal data management system of claim 3, wherein the data instructions are further executable by the processor device to display at least one of the owner's health directive for the animal or the owner's statement for treatment of the animal in response to receipt of the animal identifier information.

11. The animal data management system of claim 1, wherein the data instructions are further executable by the processor device to:

receive a second animal identifier information of a second animal and store the second animal identifier in the database;

receive second animal health care information related to the second animal's health;

store the second animal health care information in the database;

associate the second animal health care information with a location of at least one of the second animal's death or sickness; and compare a location information relating to at least one of death or sickness of the first animal in the first health care information to the location of the at least one of death or sickness of the second animal to track a cause of the at least one of death or sickness of the first animal or the second animal.

12. A method for management of animal data comprising:

registering an animal by receiving animal data and animal identification information comprising:

a first biometric identifier selected from a group consisting of: iris patterns; retinal vascular patterns; or DNA; or a vitruvian identifier selected from a group consisting of: muzzle prints;

storing the animal data and animal identification information including the first biometric or vitruvian identifier;

storing animal identification data, animal health care information, and owner information associated with the animal identifier information; and accessing the animal data upon request by a third party receiving the animal health care information related to the animal's health and owner information related to an owner of the animal corresponding to the animal identifier information;

wherein at least one of the animal health care information includes the animal data includes a health certificate with the signature of a veterinarian confirming the animal is free of an infectious disease or a veterinarian procedure performed on the animal to treat or diagnose the animal and the owner information includes at least one of the owner's health directive for the animal to inform a third party of the owner's wishes or the owner information includes the owner's statement for treatment of the animal to inform the third party of the owner's wishes.

13. The method for management of animal data of claim 12, wherein the animal health care information includes: a status of the animal; an animal owner's information; or status including at least one of whether the animal was put to sleep, whether the owner was contacted, whether the owner picked up the animal, a location of the animal, or state lines crossed by the animal.

* * * * *